United States Patent
Laffitte et al.

(12)

(10) Patent No.: US 10,780,433 B2
(45) Date of Patent: Sep. 22, 2020

(54) ACID COMPOSITION FOR PROCESSING FATTY ACIDS

(71) Applicant: ARKEMA FRANCE, Colombes (FR)

(72) Inventors: Jean-Alex Laffitte, Pau (FR); Bernard Monguillon, Bayonne (FR); Kuan Huwa Tan, Singapour (SG)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/463,548

(22) PCT Filed: Nov. 20, 2017

(86) PCT No.: PCT/FR2017/053174
§ 371 (c)(1),
(2) Date: May 23, 2019

(87) PCT Pub. No.: WO2018/096249
PCT Pub. Date: May 31, 2018

(65) Prior Publication Data
US 2019/0329229 A1    Oct. 31, 2019

(30) Foreign Application Priority Data

Nov. 25, 2016  (FR) ..................................... 16 61483
Nov. 25, 2016  (SG) ........................... 10201609943Q

(51) Int. Cl.
*B01J 31/02*   (2006.01)
*C11C 3/00*   (2006.01)

(52) U.S. Cl.
CPC .......... *B01J 31/0225* (2013.01); *C11C 3/003* (2013.01); *B01J 2231/49* (2013.01)

(58) Field of Classification Search
CPC .... B01J 31/0223; B01J 2237/49; C11C 3/003

USPC .......................................................... 554/170
See application file for complete search history.

(56) References Cited

U.S. PATENT DOCUMENTS 4,652,406 A * 3/1987 Lepper ..................... C11C 3/04
554/167
2016/0251289 A1   9/2016 Laffitte et al.

FOREIGN PATENT DOCUMENTS

| PL | 213786 B1 | 5/2012 |
|---|---|---|
| PL | 213786 B1 * | 5/2013 |
| WO | 2006/081644 A2 | 8/2006 |
| WO | 2007/050030 A1 | 5/2007 |

(Continued)

OTHER PUBLICATIONS

Aranda et al: "AcidCatalyzed Homogeneous Esterification Reaction for Biodiesel Production from Palm Fatty Acids", Catalysis Letters, vol. 122, No. 1-2, Nov. 1, 2007, pp. 20-25.*

(Continued)

*Primary Examiner* — Deborah D Carr
(74) *Attorney, Agent, or Firm* — Smith, Gambrell & Russell, LLP.

(57) ABSTRACT

The invention relates to a composition comprising:
  at least one alkane-sulphonic acid R—SO$_3$H wherein R represents a saturated, linear or branched, hydrocarbon chain comprising from 1 to 4 carbon atoms, which can or cannot be substituted by at least one halogen atom,
  at least one aryl-sulphonic acid;
  and optionally at least one solvent,
of which the proportions are as defined in the description. The invention also relates to the use of composition in a fatty acid esterification method.

14 Claims, 1 Drawing Sheet

(56) References Cited

FOREIGN PATENT DOCUMENTS

| WO | 2015/059401 A1 | | 4/2015 |
|---|---|---|---|
| WO | WO-2015059401 | * | 4/2015 |
| WO | 2015/134495 A1 | | 9/2015 |

OTHER PUBLICATIONS

International Search Report for PCT/FR2017/053174, dated Feb. 8, 2018 (6 pages with English translation).
Written Opinion for PCT/FR2017/053174, dated Feb. 8, 2018 (7 pages).
International Preliminary Report on Patentablity for International Patent Application No. PCT/FR2017053174 dated May 28, 2019 (8 pages in French with English Translation).
Aranda, D. A. G., et al. Acid Catalyzed Homogeneous Esterification Reaction for Biodiesel Production from Palm Fatty Acids. Catalysis Letters. Nov. 2007. vol. 122, No. 1-2, pp. 20-25.

* cited by examiner

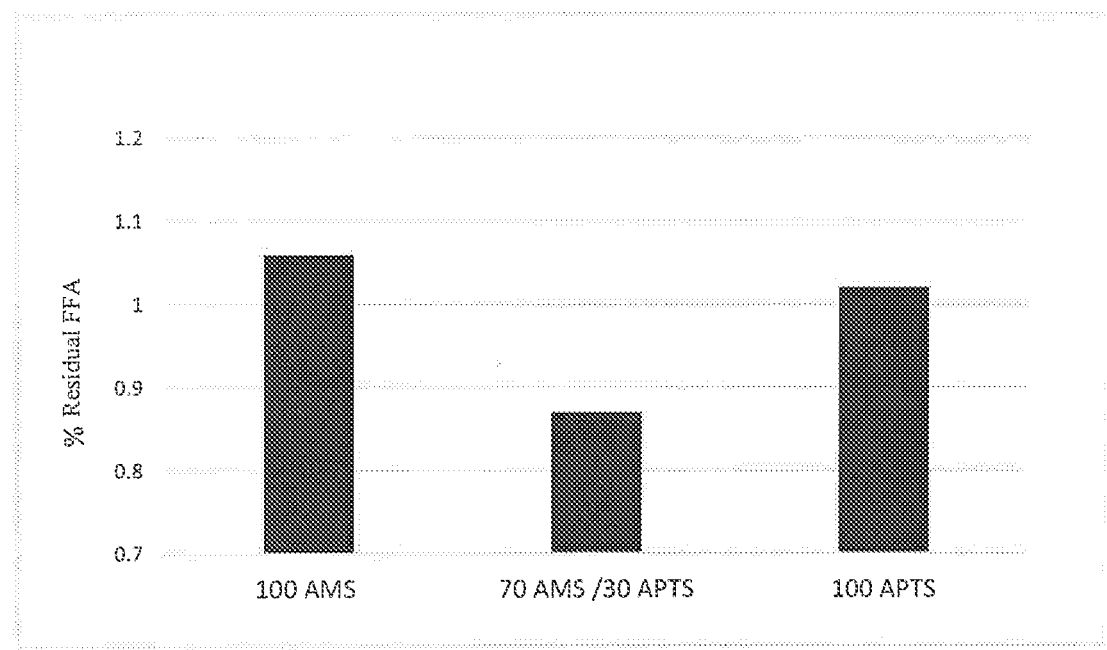
-- Figure 1 --
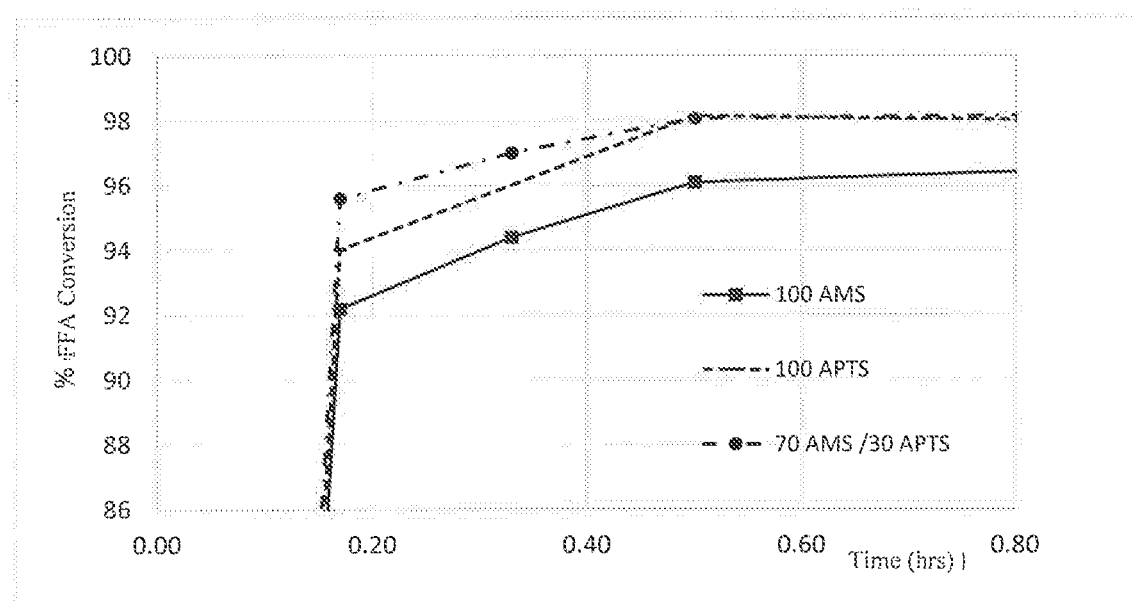
-- Figure 2 --

ACID COMPOSITION FOR PROCESSING FATTY ACIDS

The invention relates to the processing of fatty acids, particularly fatty acid esterification. The fatty acid esters obtained can thus be used as raw materials in various areas such as cosmetics or biofuel production. In particular, the invention relates to a composition of acids which can be used as a catalyst in fatty acid esterification methods.

In the esterification of fatty acids, it is often necessary to use a catalyst, for example an acid. Among the acidic catalysts used, in particular the use of paratoluene sulphonic acid is known.

For example, application WO2007005003 relates to a method for manufacturing fatty acid alkyl esters from "tall oil" containing sulphur compounds in the presence of a strong acidic catalyst such as para-toluene acid in particular.

More generally, U.S. Pat. No. 4,652,406 describes the use of aromatic sulphonic acids as catalysts to esterify free fatty acids in oils. However, as sulphonic para-toluene acid is less soluble in aqueous environments, phase separation is made more difficult.

The use of alkane-sulphonic acid is also known as acid catalyst in fatty acid esterification reactions. Thus, WO2006081644 and WO2015134495 describe the use of methane-sulphonic acid in fatty acid esterification methods.

However, as alkane-sulphonic acids are relatively expensive compounds, ways to optimise their use are being sought. Furthermore, it can be helpful to further improve the efficacy of esterification catalysts.

Therefore, one of the purposes of the present invention is to find an acid catalyst that is more effective, both in the conversion of fatty acids and from the perspective of esterification kinetics, and which is also inexpensive. To this end, the Applicant has demonstrated that a catalyst comprising at least one particular acidic composition enables, among other things, these drawbacks to be overcome.

According to another aspect, the present invention relates to a composition comprising:
at least one alkane-sulphonic acid of formula $R-SO_3H$ wherein R represents a saturated, linear or branched, hydrocarbon chain comprising from 1 to 4 carbon atoms, which can or cannot be substituted by at least one halogen atom;
at least one aryl-sulphonic acid;
and optionally at least one solvent;
wherein:
the proportion by weight of alkane-sulphonic acid in relation to the total weight of the alkane-sulphonic acid and aryl-sulphonic acid is comprised between 5% and 85%, preferably between 8% and 65%;
the proportion by weight of aryl-sulphonic acid in relation to the total weight of alkane-sulphonic acid and aryl-sulphonic acid is comprised between 15% and 95%, preferably between 35% and 92%.

The solvent can be any type known to the person skilled in the art and for example water, an organic solvent for a blend of organic solvents, or a mixture of water and one or more organic solvents.

In an embodiment of the invention, the solvent is chosen among water, alcohol and ether, preferably water and a $C_1$ to $C_3$ alcohol, and more particularly water and methanol, alone or in combination.

The proportion by weight of solvent relative to the total weight of the composition is typically comprised within a range of from 0% to 50%, preferably from 5% to 35%.

When the hydrocarbonated chain of the R group above is substituted by at least one halogen atom, said halogen atom is preferably chosen among fluorine, chlorine and bromine, preferably fluorine.

The alkane-sulphonic acid, of formula $R-SO_3H$ as previously defined, that can be used in the present invention is advantageously chosen among methane-sulphonic acid, ethane-sulphonic acid, n-propane-sulphonic acid, iso-propane-sulphonic acid, n-butane sulphonic acid, iso-butane sulphonic acid, sec-butane sulphonic acid, tert-butane sulphonic acid, trifluoromethanesulphonic acid (also known as triflic acid), and mixtures of two or more of them in any proportions, and particularly preferably methane-sulphonic acid.

The aryl sulphonic acid is chosen among benzene sulphonic acid, paratoluene sulphonic acid, naphthalene sulphonic acid, phenanthrene sulphonic acid, anthracene sulphonic acid, xylene sulphonic acid, alkyl benzene sulphonic acid, cumene sulphonic acid, and particularly preferably, para-toluene sulphonic acid.

Moreover, the acid composition according to the present invention can include one or more additives and/or filler(s), well-known to the person skilled in the art, such as those chosen, for example, among the corrosion inhibitors, fragrances, odorising agents, etc.

The present invention also relates to the use of said composition as an esterification catalyst, and more particularly in the esterification of fatty acid(s).

Finally, the invention relates to a method for manufacturing fatty acid esters comprising the following steps:
a/ introducing at least one fatty acid into a reactor;
b/ adding at least one alcohol;
c/ heating the reaction medium;
d/ introducing an acidic composition such as previously defined as a catalyst;
e/ optionally, removing the water formed during the esterification reaction; and
f/ recovering the fatty acid esters,
with step d being optionally performed at the same time as step a and/or step b, preferably at the same time as steps a and/or b.

Step e/ can be performed by heating with or without vacuum or by decanting the water/alcohol phase relative to the fatty acid ester phase.

In said method, the catalyst/fatty acid molar ratio can be comprised within a range of from 0.001 to 0.5 and particularly from 0.01 to 0.2.

The invention will be better understood by the following description, figures, and examples but is not limited to these figures and examples.

FIG. 1 represents the percentage of residual fatty acids (ordinate axis) in the organic phase after the esterification reaction depending on the nature of the acid catalyst used.

FIG. 2 represents the conversion kinetics of the residual fatty acids during the esterification stage depending on the nature of the acid catalyst used.

In said FIG. 1 and FIG. 2:
100 MSA means that the catalyst used comprises 70% pure methane-sulphonic acid and 30% water.
70 MSA/30 PTSA means that the catalyst used is the catalyst according to the invention and that it comprises:
  49% by weight of pure methane-sulphonic acid relative to the total weight of the mixture,
  26.7% by weight of the pure para-toluene sulphonic acid relative to the total weight of the mixture; and,
  24.3% water.

100 PTSA means that the catalyst used comprises 89% pure para-toluene sulphonic acid and 11% water.

The MSA used is MSA diluted to 70% by weight in water and the para-toluene sulphonic acid used is an acid diluted to 89% by weight in water.

More specifically, the invention relates to a composition comprising:

at least one alkane-sulphonic acid of formula R—SO$_3$H wherein R represents a saturated, linear or branched, hydrocarbon chain comprising from 1 to 4 carbon atoms, which can or cannot be substituted by at least one halogen atom; and at least one aryl-sulphonic acid.

"Aryl" means all aromatic radicals, such as phenyl, naphthyl, phenantryl, and anthryle radicals, preferably those comprising from 1 to 3 cycles; such radicals can be substituted by at least one alkyl comprising from 1 to 6 carbon atoms, preferably from 1 to 4 carbon atoms, such as, for example, a methyl, ethyl, propyl, butyl, preferably a methyl. If the aromatic radical is a radical substituted by at least one alkyl, it can be, for example, a tolyl, xylyl, ethyl-phenyl, or cumenyl. These acids can be used alone or in combination.

In the composition according to the invention:

the proportion by weight of pure alkane-sulphonic acid in relation to the total weight of the alkane-sulphonic acid and aryl-sulphonic acid is comprised within a range of from 5% to 85%; and the proportion by weight of pure aryl-sulphonic acid in relation to the total weight of alkane-sulphonic acid and aryl-sulphonic acid is comprised within a range of from 15% to 95%.

Preferably:

the proportion by weight of pure alkane-sulphonic acid to the total weight of alkane-sulphonic acid and aryl-sulphonic acid is comprised within a range of from 8% to 65%;

the proportion by weight of pure aryl-sulphonic acid to the total weight of alkane-sulphonic acid and aryl-sulphonic acid is comprised within a range of from 35% to 92%.

"Pure" means an undiluted compound in water or solvent.

With the composition according to the invention, the Applicant demonstrated surprising results, such as those provided as examples in this application.

It should be noted that this composition can also comprise one or more solvents, and optionally one or more additives.

"Solvent" means aqueous, organic or hydrosoluble products. Preferably, the solvent can be water, alcohol or ether, taken alone or in combination. Preferably, the solvent is water and/or a C1 to C3 alcohol. More particularly, the solvent is water, methanol or a water/methanol mixture. The content by weight of solvent relative to the total weight of the composition is comprised within a range of from 0% to 50%, and preferably from 5% to 35%

When the hydrocarbonated chain of the R group above is substituted by at least one halogen atom, said halogen atom is chosen among fluorine, chlorine and bromine, preferably fluorine.

Preferably, the alkane-sulphonic acid in the composition according to the invention is chosen among methane-sulphonic acid, ethane-sulphonic acid, n-propane-sulphonic acid, iso-propane-sulphonic acid, n-butane sulphonic acid, iso-butane sulphonic acid, sec-butane sulphonic acid, tert-butane sulphonic acid and trifluoromethanesulphonic acid (also known as triflic acid), and mixtures of two or more of them in any proportion. Preferably, the alkane-sulphonic acid is methane-sulphonic acid.

Said alkane-sulphonic acid can be used as is or in combination with one or more other components, i.e., in a formulation. Any type of formulation comprising at least one alkane-sulphonic acid may be suitable. As a general rule, the formulation comprises from 0.01% to 100% by weight of alkane-sulphonic acid, more generally from 0.05% to 90% by weight, in particular from 0.5% to 75% by weight, limits included, of alkane-sulphonic acid(s), relative to the total weight of said alkane-sulphonic acid formulation.

The formulation is, for example, an aqueous, organic or hydro-organic formulation. The formulation can be prepared in the form of a concentrated mixture, said concentrated mixture optionally being diluted prior to final use. Finally, within the meaning of the present invention, the formulation can be a pure alkane-sulphonic acid, or a mixture of pure alkane-sulphonic acids, i.e., the formulation can contain only one or more alkane-sulphonic acids, without any other additive to the formulation or any other solvent or diluent.

For example, according to an embodiment of the invention, the alkane-sulphonic acid can be diluted to 70% in a solvent, preferably in water. Preferably, the alkane-sulphonic acid is methane-sulphonic acid diluted to 70%, such as the one found on the market. For example, anhydrous methane-sulphonic acid (AMSA) can be used, or methane-sulphonic acid in aqueous solution, such as a 70% methane-sulphonic acid solution in water and marketed by Arkema under the brand name Scaleva®. A methane-sulphonic acid marketed by Arkema is also available under the name "MSA LC".

An aqueous solution of methane-sulphonic acid can also be used, such as that marketed by B.A.S.F under the name Lutropur® MSA in ready-to-use form or diluted in water in the proportions indicated above.

Preferably, the aryl-sulphonic acid is chosen among benzene sulphonic acid, para-toluene sulphonic acid, naphthalene sulphonic acid, phenanthrene sulphonic acid, anthracene sulphonic acid, xylene sulphonic acid, and cumene sulphonic acid, and particularly preferably, para-toluene sulphonic acid.

The aryl-sulphonic acid comprised in the composition can be used alone or in combination with one or more other components, i.e. in a formulation.

Any type of formulation comprising at least one aryl-sulphonic acid can be suitable. As a general rule, the formulation comprises from 0.01% to 100% by weight of aryl-sulphonic acid, more generally from 0.05% to 95% by weight, in particular from 74% to 89% by weight, limits included, of aryl-sulphonic acid(s), relative to the total weight of said formulation.

The formulation is, for example, an aqueous, organic or hydro-organic formulation. The formulation can be a concentrated mixture. Alternatively, the formulation can also be a ready-to-use formulation, i.e. one that does not need to be diluted. Lastly, according to another embodiment of the invention, the formulation can be pure aryl-sulphonic acid without any further additive to the formulation or any other solvent or diluent.

According to an embodiment of the invention, the aryl-sulphonic acid is diluted or non-diluted para-toluene acid, comprised within a range of from 60 to 100% by weight in water, such as that marketed by Huntsman. According to another embodiment of the invention, the para-toluene sulphonic acid is diluted to 89% by weight in water, such as that marketed by Sigma-Aldrich.

According to a preferred embodiment, the composition according to the invention is used as an acid esterification catalyst, preferably a fatty acid esterification catalyst.

The present invention also relates to an esterification acid catalyst, preferably a fatty acid esterification, comprising, and preferably consisting of, the acidic composition as previously defined.

The composition according to the invention is particularly useful as a catalyst, such as a catalyst for the esterification of fatty acids, either pure or combined with oils or fats, which are then called "free fatty acids", as opposed to fatty acids in the form of mono-, di- and/or tri-glycerides present in said oils and/or fats.

The fatty acid esterification reaction enables, from the condensation of an alcohol on a fatty carboxylic acid, a fatty ester and a water molecule to be obtained. "Fatty acid" means an aliphatic-chain carboxylic acid, in particular in $C_4$-$C_{36}$. Natural fatty acids have a carbon chain, saturated or unsaturated, linear or branched, comprising from 4 to 36 carbon atom(s).

According to the invention, the fatty acids can preferably be fatty acids present in oils. In this case, the esterification reaction can be followed by a transesterification reaction in the presence of light alcohol (1 to 4 carbon atoms) to obtain esters of fatty acids and glycerol; said fatty acid esters can then be used as fuel ("biodiesel").

Typically, when preparing biodiesel, if the level of residual fatty acids in oil or grease is greater than 1%, there is a risk of saponification of said residual fatty acids by reaction with the transesterification catalysts. This can be a drawback when producing biodiesel, as the soaps formed can create and emulsion and make the separation of the biodiesel and glycerol difficult or impossible.

The Applicant has thus demonstrated that, compared with alkane-sulphonic acid alone as a catalyst or compared with aryl-sulphonic acid alone as a catalyst, the mixture of at least one alkane-sulphonic acid with an aryl-sulphonic acid in the proportions claimed enables, after an esterification step, the level of residual fatty acids in the organic phase to be reduced to less than 1.1% weight, preferably 1% weight, and more particularly 0.95% weight, which is very difficult to achieve with alkane-sulphonic acid alone or aryl-sulphonic acid alone.

This low residual fatty acid content notably offers an advantage with regard to the final purity of the ester or in the transesterification step, often performed later, since the latter will consume less catalyst, usually basic catalyst, which is often expensive, and will limit the formation of soaps that disrupt the reaction.

It has also been shown that the use of the acid composition according to the invention as an esterification catalyst yields a lower amount of residual catalyst in the organic phase than the one obtained with alkane-sulphonic acid catalysts alone. This reduces the basic catalyst consumption in any subsequent transesterification in view of the production of biodiesel, for example.

Surprisingly, it has also been demonstrated that the use of the composition according to the invention improves the conversion kinetics of fatty acids compared to the use of an alkane-sulphonic acid alone or an aryl-sulphonic acid alone.

According to an embodiment of the invention, the composition according to the invention is an esterification and transesterification catalyst, thereby allowing for single-step esterification and transesterification of free fatty acids and fatty acids in the form of mono-, di- and/or tri-glycerides.

Optionally, the composition according to the invention can include one or more additives well-known to the person skilled in the art, such as those chosen among corrosion inhibitors, fragrances, odorising agents, and other additives known to the person skilled in the art.

In a preferred embodiment, the composition according to the invention comprises at least one corrosion inhibitor.

According to another preferred embodiment, the composition comprises at least one fragrance and/or odorising agent.

The composition according to the invention can be prepared according to any method known to the person skilled in the art, such as, but not limited to, the following method.

The alkane-sulphonic acid is placed in a recipient at ambient temperature. The aryl-sulphonic acid is then added in solid form and then the mixture is heated to 40° C. until completely dissolved. If a solvent and any optional additives are used, it is best to pre-mix them with the alkane-sulphonic acid before slowly adding the aryl-sulphonic acid.

The present application also concerns a method for manufacturing fatty acid esters wherein the fatty acids are esterified in the presence of the composition according to the invention.

The esterification method consists of placing a fatty acid or a mixture of fatty acids into a reactor. Alcohol is then added and the medium is heated to a temperature generally comprised within a range of from 50° C. to 200° C., more generally from 60° C. to 120° C., and preferably from 60° C. to 80° C. The composition according to the invention is preferably injected at the esterification temperature.

According to another embodiment of the invention, said composition can be added before heating. According to yet another embodiment of the invention, the alcohol and said composition can be added continuously, together or separately, when the medium has reached the esterification temperature.

According to an embodiment of the invention, said composition can be added with the fatty acid or the fatty acid mixture. According to a preferred embodiment of the invention, the fatty acid or fatty acid mixture, the alcohol and said composition are added together before heating. The esterification reaction is then performed within the previously-indicated temperature range.

During this esterification method, the composition according to the invention acts as catalyst.

The fatty acids can be of any type chosen from the fatty acids and fatty acid mixtures known to the person skilled in the art, including fatty acids from plant or animal environments, including seaweed, and more generally from the plant kingdom. These acids usually and advantageously comprise least one olefinic insaturation.

Said acids are most commonly present in vegetable oils extracted from various oilseed plants such as, but not limited to, peanuts, sunflower, rapeseed, castor. Lesquerella, olives, soybeans, oil palms, avocados, walnuts, hazelnuts, almonds, sesame, sea-buckthorn, and meadowfoam, including seaweed. They can also be obtained from land or sea animals, and in the latter case they can be obtained from mammal or fish fats, such as, but not limited to, fats from cattle, cod, whales, or seals. Finally, these acids can come from recycled used oils such as, but not limited to, used cooking oil.

As described previously, the acids in these oils are brought together with alcohol. The alcohol can be any type known to the person skilled in the art, such as the mono-alcohols, diols, triols, tetrols, etc., used alone or in combination. Preferably, the alcohol used has a molar mass comprised within a range of from 30 g/mol$^{-1}$ to 200 g/mol$^{-1}$.

According to one embodiment of the invention, the alcohol is of the $R^1$—OH type, where $R^1$ is an alkyl or aromatic, linear or branched, saturated or unsaturated chain comprising from 1 to 20 carbon atoms. Preferably, $R^1$ is a alkyl chain comprising from 1 to 10 carbon(s), particularly from 1 to 4.

According to another embodiment of the invention, the alcohol has more than one —OH function and for example the alcohol can be glycerol (propane-1,2,3-triol).

In an embodiment of the invention wherein the acid composition is used as a fatty acid esterification reaction catalyst, and in particular for free fatty acids in oils, the molar ratio of the catalyst according to the invention to the fatty acids is comprised within a range of from 0.001 to 0.5, preferably from 0.01 to 0.2. The number of moles of fatty acids is measured by acid-basic potentiometry assay and is expressed as moles per gram of fatty acids present in the starting product. This value is then multiplied by the molar ratio of the catalyst to the fatty acids to determine the amount of catalyst to be added.

According to one embodiment of the esterification method according to the invention, the alcohol/fatty acid molar ratio is comprised within a range of from 1 to 20, preferably from 4 to 10.

According to one embodiment of the invention, the fatty acid esterification reaction can be performed at any temperature but preferably at temperatures comprised within a range of from 50° C. to 200° C., more generally at temperatures of from 60° C. to 120° C., preferably from 60° C. to 80° C.

According to an embodiment of the invention, the fatty acid esterification reaction can be performed at any pressure but preferably at a pressure comprised within a range of from $10^4$ Pa (0.1 bar absolute) to $2 \cdot 10^6$ Pa (20 bar absolute), more generally comprised within a range of from atmospheric pressure to $10^6$ Pa (10 bar absolute) and most preferably at atmospheric pressure.

The reaction time for fatty acid esterification can vary considerably and is usually comprised within a range of from a few minutes to a few hours, for example from 10 minutes to 6 hours, typically from 30 minutes to 180 minutes.

The esterification reaction can be performed in batches or on a continuous basis. The catalyst according to the invention is added to the mixture or separately to the reaction medium. It can be added alone or in co-feed with the source of fatty acids (oil, animal fat, etc.) and/or the alcohol. The reaction can be performed in one or more reactors, comprised within a range of from 2 to 15, typically from 2 to 10 reactors, more typically from 2 to 5 reactors, arranged in parallel or cascaded. According to a particular embodiment, the batch method is preferred with several cascaded reactors.

It can be advantageous to carry out organic and aqueous phase separations between two reactors. In order to improve the reaction yield, the water that forms is disposed of according to any method known to the person skilled in the art, for example as it is formed, and for example, by heating. In one embodiment of the invention, removing the water can result in the removal of all or part of the solvent, particularly if the solvent is an alcohol.

According to one embodiment of the invention, the free fatty acids used come from vegetable oil to obtain biofuel, including biodiesel. In this case biodiesel is obtained after a transesterification step as described above. If a neutralization step of this biodiesel is necessary, the acid phase obtained at the end of the free fatty acid esterification reaction can be used after removal of the alcohol.

The fatty acid esterification reaction according to the invention also provides products that can be used in various fields, such as cosmetics, lubricants, agrochemistry, pharmaceuticals, cleaning, etc.

EXAMPLES

The following examples illustrate the present invention but are not limiting under any circumstances.

Method for Preparing s Composition According to the Invention

A composition is prepared, comprising:
70% by weight of methane-sulphonic acid diluted at 70% in water (49% by weight of pure methane-sulphonic acid);
30% by weight of para-toluene sulphonic acid (PTSA) diluted at 89% in water (27% by weight of pure para-toluene sulphonic acid).

The above composition is prepared from an aqueous solution at 70% by weight of MSA LC from Arkema, introduced into a double envelope reactor. The para-toluene sulphonic acid at 89% by weight is a solid that is added all at one time, at room temperature, and then the medium is heated while stirring to 40° C. until the para-toluene sulphonic acid dissolves.

The resulting composition contains, per 100 g of composition, 0.667 catalyst moles (49/96+27/172 (96 being the molar mass of the MSA and 172 being the molar mass of the PISA)), i.e., a molar mass for the formulation of 149.9 g/mol$^{-1}$ (=100/0.667).

The composition thus prepared is used as an esterification catalyst in the example below.

Example of Esterification of an Oil

An industrial blend is used, consisting of an oil comprising triglycerides and 94% by weight of free fatty acids (FFA) with a mean molecular weight of fatty acids of 268±1 g/mol$^{-1}$.

The molar methanol/FFA ratio is 8. The molar ratio of the catalyst to the FFA is equal to 0.175.

In a double-envelope reactor preheated to 50° C. and equipped with mechanical stirring, temperature probe and refrigerant, 471 g of said industrial blend comprising triglycerides and FFA at 94% by weight of FFA, i.e., 1.652 moles of fatty acid, is injected. The amount of methanol injected is determined as follows: 1.652×8×32=423 g methanol (8 molar equivalents/FAA).

The reaction mixture is heated to 70° C. and then the catalyst prepared above is injected. The amount of catalyst to be added is calculated as follows: 1.652×0.175×149.9=43.3 g of composition.

The reaction medium is stirred for 2 hours at 70° C., and then decanted and left to settle overnight at 70° C. The aqueous and organic phases are analysed according to the methods described below.

Analysis Methods

The FFA and catalyst, in the organic phase, are assayed by potentiometry as follows: about 1.5 g of organic phase is placed in a beaker which is then filled up to 50 Ml with the toluene/isopropanol/water mixture in a proportion of 500/495/5 by volume.

The potentiometric assay is performed with potash (KOH) at 0.1 mol/L$^{-1}$ in ethanol with a DG113-SC #2 electrode and T50 titrator, both from Mettler Toledo.

The assay is used to determine accurately, on the one hand, the amount of residual catalyst in the organic phase in moles per gram, and on the other hand the content in residual fatty acids in the organic phase in % by weight.

The acid-base assay enables 2 potential jumps to be obtained: the first jump corresponds to the catalyst and the second jump corresponds to the residual fatty acids.

Results

On the one hand, the assays described above measure the percentage of residual FFA in the organic phase that will then undergo transesterification. These results are shown in FIG. 1.

The results show that the mass percentage of residual FFA is 1.2 with MSA alone, 1.02 with PTSA alone, and 0.87 with the composition according to the invention.

With the composition according to the invention, a percentage of residual FFA is obtained that is less than that obtained with MSA alone or PTSA alone.

On the other hand, the FFA conversion kinetics is improved compared to the use of each acid alone as shown in FIG. 2. Indeed, it was found that the composition according to the invention resulted in faster ester conversion kinetics.

The invention claimed is:

1. A catalytic composition comprising:
   at least one alkane-sulphonic acid of formula R—SO$_3$H wherein R represents a saturated, linear or branched, hydrocarbon chain comprising from 1 to 4 carbon atoms, which can or cannot be substituted by at least one halogen atom;
   at least one aryl sulphonic acid;
   and at least one solvent;
   wherein:
   the proportion by weight of alkane-sulphonic acid in relation to the total weight of the alkane-sulphonic acid and aryl-sulphonic acid is comprised between 5% and 85%
   the proportion by weight of aryl-sulphonic acid in relation to the total weight of alkane-sulphonic acid and aryl-sulphonic acid is comprised between 15% and 95%.

2. The composition according to claim 1 wherein the solvent is chosen among water, alcohol and ether, alone or in combination.

3. The composition according to claim 1 wherein the solvent is water or a C$_1$ to C$_3$ alcohol, alone or in combination.

4. The composition according to claim 1 wherein the solvent is water or methanol, alone or in combination.

5. The composition according to claim 1 wherein the proportion by weight in solvent relative to the total weight of the composition is comprised within a range of from 0% to 50%, preferably from 5% to 35%.

6. The composition according to claim 1, wherein the alkane-sulphonic acid is chosen from methane-sulphonic acid, ethane-sulphonic acid, n-propane-sulphonic acid, iso-propane sulphonic acid, n-butanesulphonic acid, iso-butane-sulphonic acid, sec-butane sulphonic acid, tert-butane sulphonic acid, trifluoro methane-sulphonic acid, and mixtures of two or more of them in any proportions.

7. The composition according to claim 1 in which the alkane-sulphonic acid is methane-sulphonic acid.

8. The composition according to claim 1 wherein the aryl-sulphonic acid is para-toluene sulphonic acid.

9. The composition according to claim 1 comprising at least one corrosion inhibitor.

10. The composition according to claim 1 comprising at least one fragrance or one odorising agent, alone or in combination.

11. In a catalytic method for manufacturing fatty acid esters wherein the improvement comprises the composition according to claim 1 as an esterification catalyst.

12. A method for manufacturing fatty acid esters comprising the following steps:
   a/ introducing at least one fatty acid into a reactor;
   b/ adding at least one alcohol;
   c/ heating the reaction medium;
   d/ introducing a composition according to claim 1 as a catalyst;
   e/ optionally, removing the water formed during the esterification reaction; and
   f/ recovering the fatty acid esters,
   with step d being optionally performed at the same time as step a and/or step b, preferably at the same time as steps a and/or b.

13. The method according to claim 12 wherein the catalyst/fatty acid molar ratio is comprised between 0.001 and 0.5 and particularly between 0.01 and 0.2.

14. The composition of claim 1 wherein the proportion by weight of alkane-sulphonic acid in relation to the total weight of the alkane-sulphonic acid and aryl-sulphonic acid is comprised between 8% and 65% and the proportion by weight of aryl-sulphonic acid in relation to the total weight of alkane-sulphonic acid and aryl-sulphonic acid is comprised between 35% and 92%.

* * * * *